United States Patent [19]
Cosgrove, Jr. et al.

[11] Patent Number: 4,533,346
[45] Date of Patent: Aug. 6, 1985

[54] SYSTEM FOR AUTOMATIC FEEDBACK-CONTROLLED ADMINISTRATION OF DRUGS

[75] Inventors: Robert J. Cosgrove, Jr., Birmingham, Ala.; Victor F. Smolen, West Lafayette, Ind.

[73] Assignee: PharmaControl Corporation, Englewood Cliffs, N.J.

[21] Appl. No.: 411,473

[22] Filed: Aug. 25, 1982

Related U.S. Application Data

[63] Continuation of Ser. No. 239,818, Feb. 19, 1981, abandoned, which is a continuation of Ser. No. 52,242, Jun. 26, 1979, Pat. No. 4,280,494.

[51] Int. Cl.³ ............................................. A61M 5/00
[52] U.S. Cl. ...................................... 604/66; 128/731
[58] Field of Search ............................. 604/65, 66, 67; 128/731

[56] References Cited

U.S. PATENT DOCUMENTS

| | | | |
|---|---|---|---|
| 2,690,178 | 9/1954 | Bickford | 604/66 |
| 3,837,339 | 9/1974 | Aisenberg et al. | 604/66 |
| 3,882,861 | 5/1975 | Kettering et al. | 604/66 |
| 4,055,175 | 10/1977 | Clemens et al. | 604/66 |
| 4,151,845 | 5/1979 | Clemens | 604/66 |

OTHER PUBLICATIONS

Fukui et al., "Proceedings of the San Diego Biomedical Symposium", 1974, pp. 273-278.

Primary Examiner—William E. Kamm
Attorney, Agent, or Firm—Pennie & Edmonds

[57] ABSTRACT

A system for automatic feedback controlled administration of drugs (SAFCAD) is disclosed for the control of administration of drugs responsive to real-time processed physiological or pharmacological signals. Control apparatus implemented by analog, digital, or optimal-adaptive digital means is described using various combinations of proportional, integral and derivative control loop processes. A preferred digital embodiment uses optimal-adaptive, proportional-integral control which includes on-line physiological system modeling and control loop parameter tuning for the administration of anesthetics such as thiopental.

31 Claims, 9 Drawing Figures

SYSTEM FOR AUTOMATIC FEEDBACK-CONTROLLED ADMINISTRATION OF DRUGS

This is a continuation of application Ser. No. 239,818, filed Feb. 19, 1981, now abandoned, which is a continuation of U.S. Ser. No. 052,242, filed on June 26, 1979, now U.S. Pat. No. 4,280,494.

BACKGROUND OF THE INVENTION

The present invention relates generally to closed loop control systems for administering a drug chemical to a subject, and more particularly to a control system for administering a drug wherein selected parameters of the control loop are dynamically varied in real time, responsive to the sensed physiological parameter(s) and the process reaction relationship thereby exercising optimally adaptive feedback control of drug administration.

Over the last two decades, it has become widely recognized that a dose of drug chemical does not, in itself, constitute safe and effective therapy in clinical usage. The manner in which the drug is administered to the body by drug-delivery systems can be equally important, if not more so. Therefore, drugs are marketed and employed not as pure chemical substances, but as drug products, which constitute drug-delivery systems.

Prior art drug-delivery systems have been broadly defined as chemical, mechanical, or electromechanical devices designed to input drugs to the systemic circulation or to specific target sites in the body at predetermined, controlled rates. If the drug input is not obtained at a predetermined controlled rate, however, the drug-delivery system can be best described as a drug-dump system. Most drug products currently on the market fall into the latter category in that the time course of their release (for example, via dissolution from a tablet) is generally fortuitous rather than being predetermined or designed on the basis of rational pharmacological criteria. The interested reader is referred to the article, "Bioavailability and Pharmacokinetic Analysis of Drug Responding Systems" (1978) by V. F. Smolen for an overview discussion of this subject. Despite extensive research and development efforts, very few chemical drug-delivery systems readily lend themselves to predetermined and controlled rates of drug release in vivo. In all cases, drug-release rates depend on the kinetic process of diffusion and/or on chemical reaction (hydrolysis), both of which are difficult to predict or control in a complex and often uncertain biologic environment within which the drug-delivery system must perform. Thus, controlled drug release is relatively difficult to attain by means of chemical systems, and up to the present time, such systems have been only partially successful.

Some drugs, such as intravenous anesthetics, hypotensive agents, and insulin, can require continuous readjustment of dose rates in response to the development of tolerances or hypersensitivities, or in accordance with changing pathophysiologic conditions or dietary factors. Such individualized dosage adjustment is especially important for rapidly acting drugs that have a narrow therapeutic range. What is needed to solve the problem of interpatient drug-response variability are closed loop drug products that release drugs to their physiologic sites of action in response to the patient's momentary therapeutic needs, rather than drug products that merely release quantities of drugs at standard rates that are predetermined by the product design and formulation.

Illustrative prior art devices of the closed loop type are disclosed in U.S. Pat. No. 2,690,178 to Bickford and in U.S. Pat. No. 4,080,966 to McNally et al. The Bickford '178 patent teaches the use of a proportional control circuit for the intermittent administration of drugs to maintain anesthesia, based on the decrease observed in the energy of the electroencephalographic (EEG) pattern with increasing depth of anesthesia. While this teaching represented a major advance in the the art of controlled administrations of drugs, the actual implementation of the control system was somewhat primitive, and it was not widely accepted for practice in anesthesia. Also contributing to its limited acceptance with the increasing popularity of anesthetics other than ether and thiopental described in the disclosure; and the fact that the EEG patterns associated with these new drugs were not as directly related to anesthesia levels as was the pattern of ether and thiopental.

The McNally et al '966 patent discloses an analog implemented closed loop control system used to regulate the blood pressure of mammals utilizing controlled infusion of drugs responsive to continuously monitored arterial blood pressure. The disclosed embodiment teaches the use of proportional plus derivative (plus integral) controlling techniques and recites the use of both liquid hypertensive agents, or liquid hypotensive agents into the circulatory systems. Additional U.S. patents which disclose the use of closed loop techniques for administering medications of various kinds are U.S. Pat. No. 4,078,562 to Friedman; and U.S. Pat. No. 4,055,175 to Clemens et al. The Friedman patent discloses the use of periodically administering a pharmaceutical such as oxytocin or the like, to induce labor in a pregnant woman; while the Clemens et al patent describes an apparatus for controlling blood glucose by selected infusion of insulin and/or glucose responsive to a computer controlled output signal.

While a good deal of effort has been expended in the area of feedback drug administration, it is clear that a significant amount of work remains to be done, particularly with respect to the use of a wider range of drugs and in higher precision drug-delivery systems. Recent work resulting in the invention disclosed hereinbelow, has resulted in a system for automatic feedback-controlled administration of drugs (SAFCAD) for thiopental anesthesia that adapts to changes in patient responsiveness to the drug, thus maintaining an optimum controller action. A detailed description may be found in Cosgrove, R. J. and Smolen, V. F., "Systems for Automatic Feedback-Controlled Administration of Drugs: Analog and Digital Optimal-Adaptive Control of Thiopental Anesthesia," *Innovations in Biomedicine, Proc. San Diego Biomedical Symposium*, ed. Martin, J. North Hollywood, CA, Western Periodicals, 1978. This SAFCAD for thiopental is considered useful not only for surgical anesthesia, but also for the treatment of cerebral ischemia resulting from brain injury, stroke and post-circulatory-arrest encephalopathy. In the latter group of conditions, long-term infusion of a barbiturate such as thiopental may be necessary in comatose patients to minimize brain swelling. The mortality rate of head-injured patients undergoing barbiturate treatment in this manner was reported to be 35% of that associated with untreated head-injured patients. However, such barbiturate therapy requires meticulous patient monitoring, sometimes for several weeks or even longer. Use of a barbiturate SAFCAD could reduce the need for such monitoring, thereby rendering barbiturate therapy practical on a large scale. The present invention discloses precisely such a system.

SUMMARY OF THE INVENTION

It is therefore a primary object of the present invention to provide improved apparatus for the administration of drugs to subjects; and apparatus which overcomes the disadvantages of the prior art system.

A further object of the present invention is to provide a SAFCAD for the administration of drugs to subjects wherein a real-time evaluation of key physiological parameter(s), and determination of the drug/subject system model provided the basis for precision control of the particular agent employed.

Another object of this invention is to provide a high precision SAFCAD comprised of readily available components, and particularly to provide a range of analog and digital embodiments using these components.

It is a further object of this invention to provide advanced apparatus for precise, stable infusion of thiopental not only for surgical anesthesia, but also for the treatment of cerebral ischemia resulting from brain injury, stroke, and post circulatory-arrest encephalopathy where long-term infusion as indicated in comatose patients to minimize brain swelling.

In a preferred embodiment of the present invention, a digital system using a commercially available minicomputer implements an on-line adaptive control loop for the precise administration of thiopental responsive to a processed version of the subject's EEG signals, thereby enabling a stable anesthesia level to be accomplished by the clinician.

BRIEF DESCRIPTION OF THE DRAWINGS

Additional objects and advantages of the invention will become apparent to those skilled in the art as the description proceeds with reference to the accompanying drawings wherein.

DETAILED DESCRIPTION OF THE PREFERRED EMBODIMENTS

Figure 1:
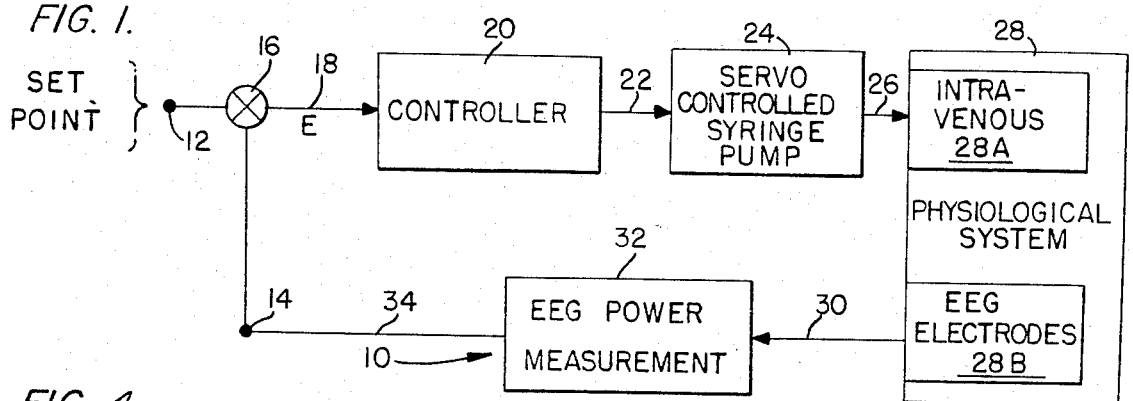
FIG. 1 is a block diagram of a basic closed loop control system for administration drugs to a subject.

Referring now to FIG. 1, there is shown a simplified block diagram of a basis closed loop system for administering drugs to a subject. The term subject is used herein to include all physiological systems including human patients, as well as lab animals. The basic closed loop system 10 is configured, conventionally, to accept a desired input set point via an input node 12 and a processed parameter related to the controlled variable via a feedback node 14, both of which are applied to an algebraic summing node 16. The output of the summing node 16 is an error signal E which is applied via a line 18 to an input of a controller 20, whose output is in turn routed via a line 22 to the input of a servocontrolled syringe pump 24. The output of the servocontrolled syringe pump 24 is routed via a line 26 and is applied to subject 28 via an intravenous (i.v.) connection 28A. An array of electroencephalograph (EEG) electrodes 28B are appropriately positioned on the subject 28 and deliver their composite output via a line 30 to an EEG power measurement means 32. The output from the EEG power measurement 32 represents the aforementioned processed control variable, and is applied via a line 34 to the feedback node 14 thereby closing the control loop.

A brief overview description of the operation of this basic system is facilitated with continued reference to FIG. 1. For present purposes, it is not necessary to detail precisely what is the controlled variable in this basic system, other than to observe that the application of a drug chemical, or agent, to the subject via the intravenous connection 28A provides the excitation to, and the EEG electrodes 28B provide a corresponding response from, the controlled variable. Illustratively, the description is presented for the case where the drug is an anesthetic, such as thiopental, and the processed EEG response is the measure of the level of anesthesia achieved. A predetermined, control level is first determined by the clinician/operator based on the specifics of the drug-physiological conditions involved, and is inserted as the control system input order, designated as the set point. The set point would correspond to a desired level of anesthesia for the subject. An error signal E would immediately reflect a difference between the ordered set point on the input node 12 and a normal (not anesthetized) processed EEG feedback signal on the feedback node 14, and would cause the controller 20 to provide an actuating signal to the servocontrolled syringe pump 24. The servocontrolled syringe pump 24 would begin to precisely infuse the thiopental from a reservoir (not shown) into the subject via the i.v. connection 28A, and a corresponding alteration of the subject's EEG activity would follow subsequently. As the subject's EEG activity becomes reflected in appropriate feedback levels via the EEG power measurement 32, the actual error signal is reduced, and, in the ideal steady state condition, the control system 10 can maintain continuous and precise control over the subject's level of anesthesia responsive to the operator's ordered set point. As discussed earlier, it has been determined that the total output power of the EEG signal from both humans and animals, provides a useful indication of the subject's anesthesia level. The pharmacokinetic and control system problem is, however, far from being as simple as described above and some of the basic difficulties are described in the aforementioned Bickford patent.

It is clear that the closed loop control system of FIG. 1 can be implemented in a wide variety of means including the use of classical analog circuitry, digital circuitry, or hybrid mixes of the two; and that the digital configurations could be accomplished using the full range of technologies from discrete solid state circuitry to the use of VLSI, minicomputers, or general purpose digital computers. Beyond the type of implementations used, a variety of control techniques may also be embodied in the hardware. Laboratory versions of the present invention have been built using proportional-integral controllers, and derivative-mode controllers and other control techniques, such as proportional-integral-derivative controllers, and basic proportional controllers have also been assessed. A preferred embodiment utilizing an adaptative digital mode will be described as representing the best operating mode known of the various configurations tested. Also, in addition to EEG measurements, a number of other physiological measurements can be used separately, or in combinations, to assess the depth of anesthesia for use as the feedback variable in the present invention. The other measurements may include: electrocardiographic; respiratory; pupilary; blood-pressure; body temperature; reflexive peripheral vascularity; blood or other body fluid drug agent; or metabolite concentration; biochemical concentration; and the like.

The automatic adaptive controller, herein disclosed, can be used for administration of many classes of drugs and can be used with many physiological and pharmacological response signals and processed response signals. Some of the classes of drugs which can be administered by SAFCAD include injectable anesthetics, such as thiopental, hexobarbital, methohexital, methitural, thiamylal and others, gaseous inhalation anesthetics, such as nitrous oxide, ethylene, cyclopropane and other, volatile anesthethics, such as halothane, methoxyflurane, diethyl ether, divinyl ether, halopropane, fluroxene and others, antihypertensive agents, such sodium nitroprusside, trimethaphan and others, barbiturates, such as secobarbital, phenobarbital, barbital and others, natural hormones, such as insulin, glucagon, oxytocin, somatostatin, thyroxin, parathyroid hormone, leutinizing hormone, testosterone, progesterone and others, synthetic hormones, such as norethisterone and others, anticholinesterase drugs, parasympathomimetic agents, sympathomimetic agents, atropinic agents, neuromuscular blocking agents, such as d-tubocurarine, succinylcholine and others, vasodilators, such as the organic nitrites, antiarrhythmics, such as quinidine, procainamide, digitalis, and others, and other drugs and nutrients, salts, buffers, fluids, serum, plasma, whole blood and the like, which may not ordinarily be considered drugs, but which can be administered at controlled rates to affect nutrition, heart rate, blood pressure, cardiac output, fluid volume, osmotic pressure, pH of the blood and other physiologic fluids.

The physiological measurments for response signals which can be used in the optimal control system include those indicated above as being of use in the control of anethesia. These signals can be of utility in assessing the response to other drugs. In addition other useful physiological parameters include electromyography, electroretinography, galvanic skin response, the concentration in any physiological fluid of oxygen, carbon dioxide, drug, metabolite, biochemical, salt, hydronium ion, hydroxyl ion and so forth, the osmotic pressure of any physiological fluid, and many other physiological parameters. The physiological measurements which are useful include evoked physiological measurements, wherein the response measured is elicited by an external stimulus. The present invention includes in its spirit and scope automatic adaptive control of administration of any drugs, chemicals, compounds and substances by analysis of any physiological parameters which can be measured by any means.

Figure 2:
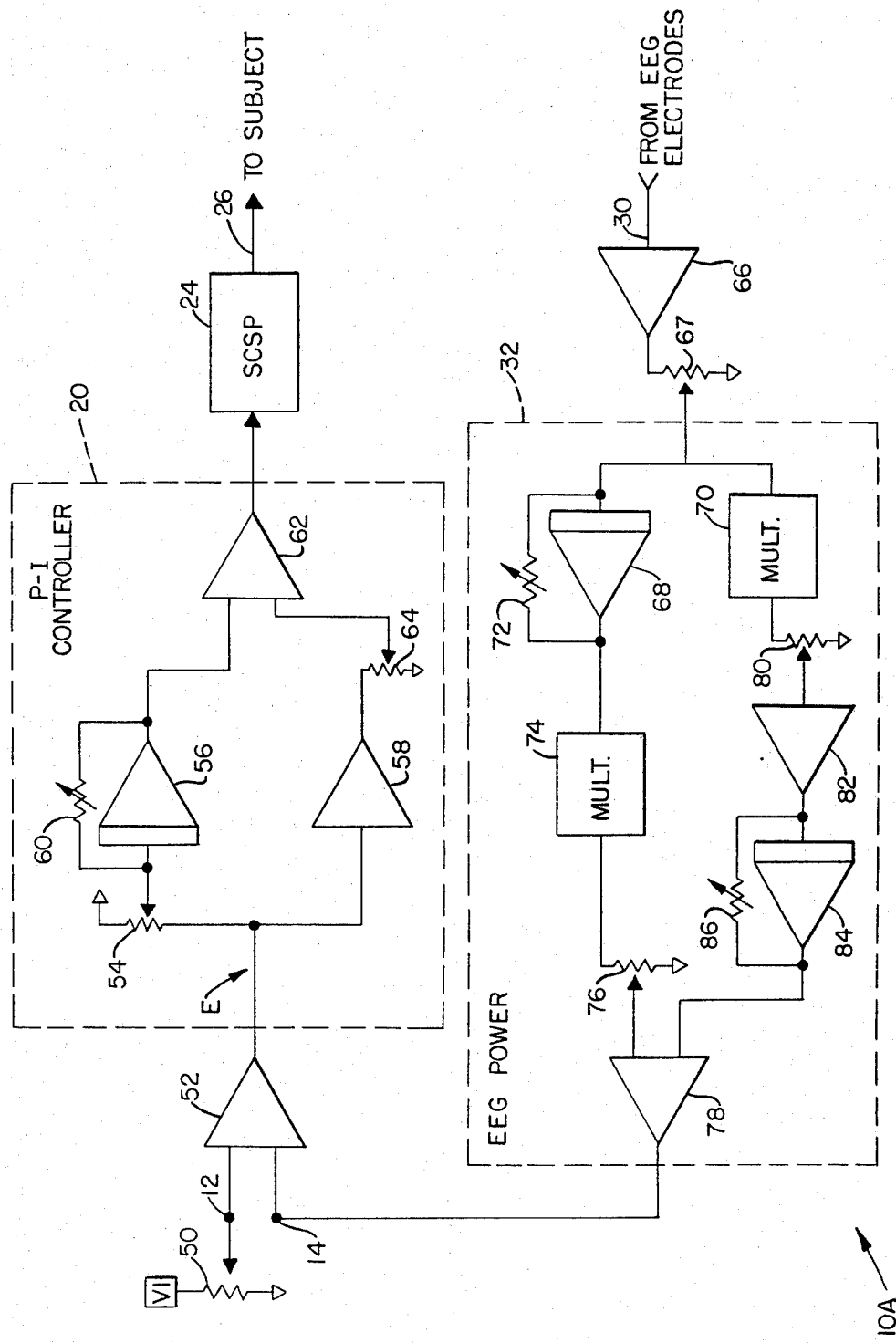
FIG. 2 is an analog implementation of a SAFCAD using a proportional-integral control loop technique.

Referring now to FIG. 2, there is shown an analog implementation of an intermediate level closed loop control system for administering drugs using, illustratively, a proportional-integral (PI) controller. The system may be assembled using a small analog computer commercially available as Electronics Associates Model EAI MiniAC, and will serve as a baseline model which will later be discussed in terms of a preferred digital embodiment. Brief reference to FIG. 1 shows the I/O of FIG. 2 to be structured substantially the same—having an input node 12, a feedback node 14, a servo-controlled syringe pump outlet line 26, and an EEG electrode output line 30. The analog PI control system 10A has as its set point input a potentiometer 50 connected between a stable potential V1 and a system reference ($\frac{1}{\nabla}$), and having its moveable arm routed to the input node 12, and thereafter to a first input of an operational amplifier configured as a voltage comparator 52. The second input to the comparator 52 is the processed controlled variable signal applied via the feedback node 14. The output of the comparator 52, designated as the error signal E, is routed first to a potentiometer 54 whose moveable arm is routed to the input of an op amp integrator 56; and also to the input of an op amp amplifier 58. The integrator 56 has a variable resistor 60 serving as part of its feedback network, and has its output routed to a first input of a summing amplifier 62. The output of amplifier 58 is routed to a potentiometer 64 whose moveable arm is routed to a second input of the summing amplifier 62. The output of summing amplifier 62 is routed as the actuating signal to the servo-controlled syringe pump 24, which may be of a type commercially available as Harvard Model 994. The upper branch of the controller 20, which includes the integrator 56, provides the integral portion of the control signal; while the lower branch which includes the amplifier 58 provides the proportional portion. The potentiometer 54 determines the relative weights of integral to proportional control, and the variable resistor 60, in combination with the integrator 56, adjusts the filtered integral error. The potentiometer 64 determines the proportional gain, Kc, of the controller. While not specifically shown, the ouput of amplifier 62 may be buffered as required to drive the pump 24 (and other loads, or recorders not shown) without output loading. Also, for clarity of exposition, the various other routine components normally associated with op amp circuitry have been omitted.

The EEG signal is routed via the line 30 to an op amp amplifier 66, and thereafter to a potentiometer 67 whose moveable arm is routed first to the input of an op amp integrator 68; and also to the input of a multiplier 70. Integrator 68 has a variable resistor 72 serving as part of its feedback network and has its output routed to the input of a multipler 74. The output of multiplier 74 is routed to a potentiometer 76 whose moveable arm is routed to a first input of a summing amplifier 78. The output of multiplier 70 is routed to a potentiometer 80 whose moveable arm is routed to the input of an op amp amplifier 82, and thereafter to the input of an op amp integrator 84. The integrator 84 has a variable resistor 86 serving as part of its feedback network, and has its output routed to a second input of the summing amplifier 78.

In operational use, the amplifier 66 is adjusted to compensate for major differences in EEG signal amplitude between subjects. The upper branch of the EEG power measurement block 32 compensates for any DC drift in the EEG signal by forming the square of the exponentially mapped past (EMP) estimate of the mean EEG voltage. Integrator 68 produces the EMP estimate of the EEG signal and multiplier 74 squares this quantity. The result of this (upper) branch is the function:

$$f_1(t) = K3 \left[ K1 \cdot A1 \int_{-\infty}^{t} EEG(T) \cdot e^{-P2(t-T)} dT \right]^2 \quad (1)$$

where the constants are related to the variable resistors and potentiometers as follows—K1 is determined by the setting of potentiometer 67; K2 by the variable resistor 72; K3 by the potentiometer 76; and K1 is the gain of amplifier 66.

Multiplier 70 squares the EEG signal to produce a normalized (into one ohm) EEG power. Potentiometer 80 serves as a channel gain adjust and integrator 84 provides an estimated mean power determination of the EEG signal power. The result of this (lower) branch is the function:

$$f_2(t) = A2 \cdot K4 \int_{-\infty}^{t} [A1 \cdot K1 \cdot EEG(T)]^2 \cdot e^{-K5(t-T)} dT \quad (2)$$

where the constants are related to the variable resistors and potentiometers as follows—K4 is determined by the setting of potentiometer 80, K5 by variable resistor 86; and A2 is the gain of amplifier 82. Amplifier 78 sums these two signals together to precisely form the DC-corrected EEG power, and the output of amplifier 78 constitutes the fed back processed signal applied to the feedback node 14.

The action of the PI controller is described in Equation 3, where M is the i.v. dose rate, $K_c$ is the overall controller gain, $\epsilon$ is the error signal (i.e., the difference between the desired set-point and the actual response), and $T_i$ is the integral time.

$$M = K_c \left( \epsilon + \frac{1}{T_i} \int \epsilon \, dt \right) \quad (3)$$

Optimal dynamic response of this control system represents a compromise between the sluggishness of overdamping and the instability of excessive sensitivity. For a PI controller, one achieves this compromise by tuning the controller to obtain optimal values for $K_c$ and $T_i$ settings. Achievement of an acceptable set of values will depend on the open-loop dynamic-response behavior of the specific system to be controlled and on the criteria that are considered capable of providing acceptable response dynamics when the loop is closed and the feedback controller is inserted (as shown in FIGS. 1 and 2). The Cohen-Coon or process-reaction-curve method is employed to tune the PI controller on-line. The interested reader is referred to Cohen, G. H. and Coon, G. A., "Theoretical Considerations of Retarded Control," Trans. ASME, Vol. 74, 1953, p. 827, for further description of the technique. The Cohen-Coon method assumes that the impulse response of the system to be controlled can be approximated by a first-order time-delay model. In the present case, this assumes that, following a unit bolus dose, the EEG change would occur after a time delay ($T_d$) and would then decline to its original value by following a monoexponential decay curve. The assumed impulse-responsive curve—i.e., the assumed weighting function, G(t)—can be described in the time domain using Equation 4 below.

$$G(t) = \frac{S}{M} \exp\left(-\frac{S}{B_u} t\right) u(t - T_d) \quad (4)$$

In the above equation, $B_u$ is the ultimate gain and $u(t-T_d)$ symbolizes a unit-step function with a time delay $T_d$, M is the dose rate, S is the slope of the response curve at its point of inflection, $S/B_u$ is the first-order time constant, and t represents time.

Equations 5 and 6 may be used to compute optimal values for PI controller settings. As described in the aforementioned Cohen and Coon paper, these controller settings should theoretically provide a response-versus-time curve that has a minimal area, minimal offset from the desired set point level, and a one-quarter decay ratio (that is to say, each successive amplitude of the oscillations in the closed-loop response to a step-disturbance curve should be 25% of the previous peak).

$$K_c = \frac{M}{T_d S} \left( 0.9 + \frac{T_d S}{12 B_u} \right) \quad (5)$$

$$T_i = 3 T_d \frac{(10 B_u + T_d S)}{(9 B_u + 20 T_d S)} \quad (6)$$

It should be noted that the above equations must be considered as first-order approximations only, and empirical adjustment is always required to truly optimize physiological control systems.

Summarizing then, amplifier 52 serves as the closed loop control system comparator and the setting of the potentiometer 50 constitutes the clinician/operator inserted set point. The error signal E is formed by the comparator 52 and is applied to the input of the controller, shown in dashed lines as the block 20. The error signal is split to form proportional and integral components of the actuating signal and the setting of potentiometer 64 determines the proportional gain, $K_c$, of the controller 20. The actuating signal controls the pump rate of the servocontrolled syringe pump 24 which administers a precisely controlled flow of drug agent to the subject. The EEG signals are manipulated in the EEG power measurement block 32 to form a feedback signal corresponding to a desired processed version of the controlled variable, namely a quantity representative of the subject's total EEG signal power, which reflects the results of the drug agent supplied.

Figure 3:
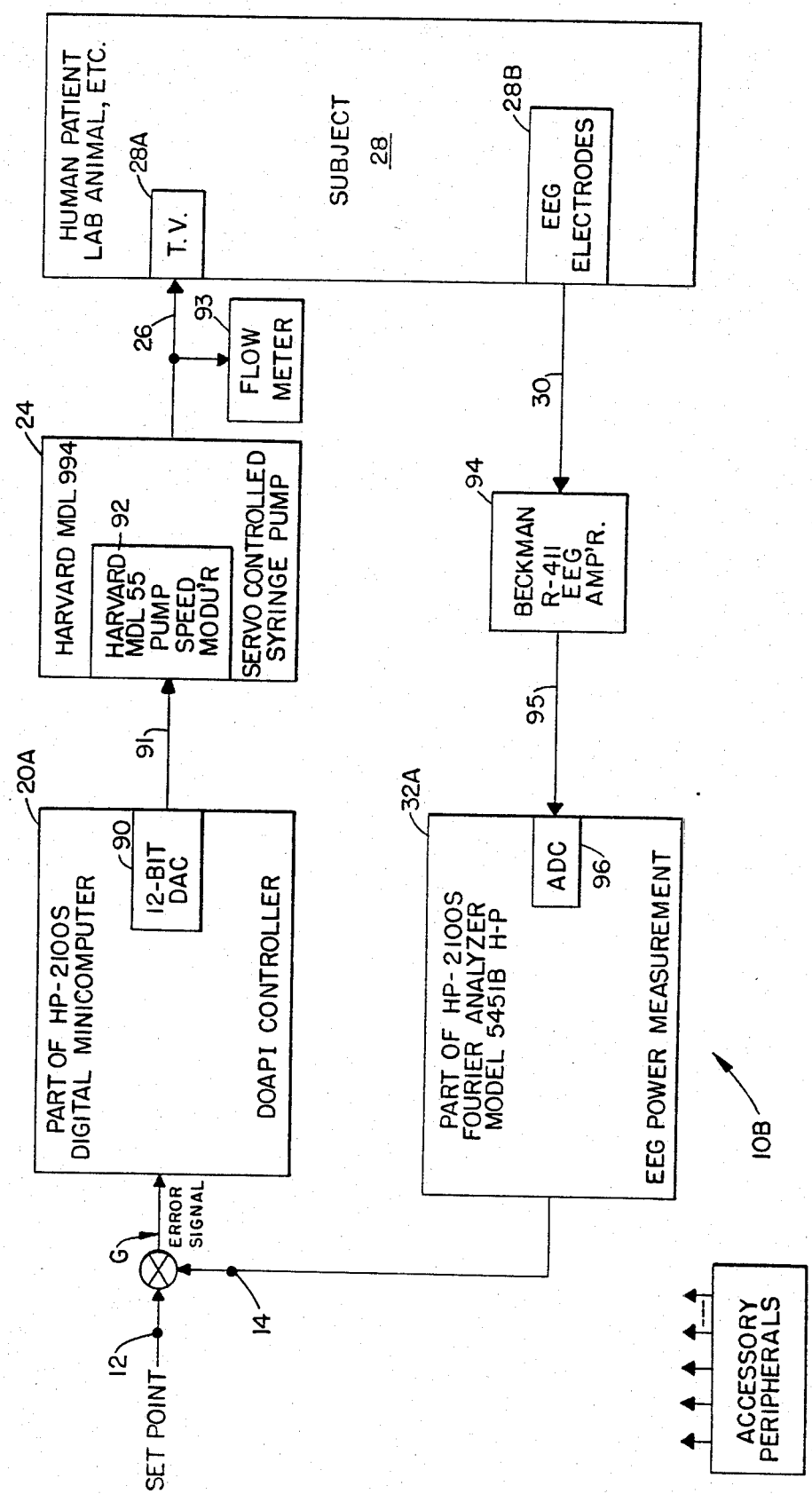
FIG. 3 shows a preferred embodiment of a digital control system for administering liquid thiopental for the precise control of anesthesia in subjects.

Referring now to FIG. 3, there is shown a detailed block diagram of a digital closed loop control system for administering drugs to a subject which can be patterned to emulate the analog control system described in connection with FIG. 2. While the primary description of the embodiment of FIG. 2 was directed to a proportional-integral (PI) type of controller, a number of other analog controllers (a P type; a PD type; and a PID type) have been assembled for evaluation purposes. Therefore, the description of this digital system will parallel the description of the analog PI controller type, but it should be noted that a digitally-implemented control system may be made to emulate any of the controller types. Actually, the flexibility of properly assembled digital systems to take on widely varying configurations without an undue amount of effort is one of the major advantages offered by this particular embodiment.

This preferred digital embodiment is implemented using a digital minicomputer and incorporates the optimal-adaptive control technique to enhance the dynamic performance of drug administration. For the most part, the digital implementation of the various blocks of FIG. 3 comprising the control loop 10B may represent functionally equivalent elements to those shown in FIG. 2. That is, the controller 20A and the EEG power measurement means 32A comprise a small digital computer programmed to perform the integrations, summations, and multiplications detailed in connection with the analog PI controller. As before, the digital embodiment is shown as having an input node 12, a feedback node 14, a servocontrolled syringe pump output line 26, and an EEG electrode output line 30. The digital error signal E, which is provided from the algebraic summary node 16 and represents the difference between the digitally inserted set point value and a digital representation of the EEG signal power, is applied to an input of the digital controller 20A where it is processed. The digital controller 20A may be of the type commercially available as the Hewlett Packard minicomputer model 2100S, programmed to execute the steps summarized in the flow chart of FIG. 4. The output from the controller 20A is converted into an analog voltage suitable for driving the servocontrolled syringe pump 24 by a 12-bit digital-to-analog converter (DAC) 90, which may be of the type generally available commercially. The output of the DAC 90 is routed via a line 91 to the input of a pump speed modulator 92, commercially available as a Harvard Apparatus Model 55. The modulator 92 serves to interface the precision DC voltage on the line 91 to the proper voltages required by the servocontrolled syringe pump 24. The servocontrolled syringe pump 24 may be of the type commercially available as Harvard Apparatus Infusion/Withdrawal Pump Model 944, which is capable of providing constant and automatic precisely controlled infusion flow rates. To monitor this precisely controlled continuous flow, a precision flow measurement device 93 is positioned to sense the flow rate in the output line 26. This device may be of a differential pressure type commercially available as a Whittaker Corp. Model CD10. Thereafter, the line 26 routes the flow of the drug agent to the subject where it is infused intravenously at a site appropriate for the agent in use.

The composite output signal from the EEG electrode array is applied via the line 30 to an EEG amplifier 94, which may be of the type commercially available as Beckman Dynagraph Models R-411 and R-511. The EEG signal, amplified to a suitable level, is routed via a line 95 to the input of an analog-to-digital converter (ADC) 96 and subsequently into the EEG power measurement section 32A. The ADC 96 may be of the type commercially available as Hewlett Packard Model 5466B, and the EEG power measurement 32A is implemented using a portion of the Hewlett Packard Model 2100S minicomputer operating in conjunction with an analysis system based on a Hewlett Packard Fourier Analyzer, Model 5451B. The output of the EEG power measurement 32A represents a near real time measurement of the EEG power in the subject's response, and is routed to the feedback node 14 thereby closing the control loop as before. A pseudorandom binary signal (PRBS) generator 97 is positioned within and controlled by a portion of the HP-2100S minicomputer and serves to provide a test signal for randomly infusing small amounts of thiopental via the servocontrolled infusion pump 24.

A number of peripheral devices may be used in conjunction with this digital implementation for both operational, and test and evaluation purposes. These are designated generally by the block 98, and may include a system input/output TTY terminal; a line printer; a digital plotter; a CRT display; a paper tape photoreader; recorders of various types; and other similar supporting devices.

Figure 4:
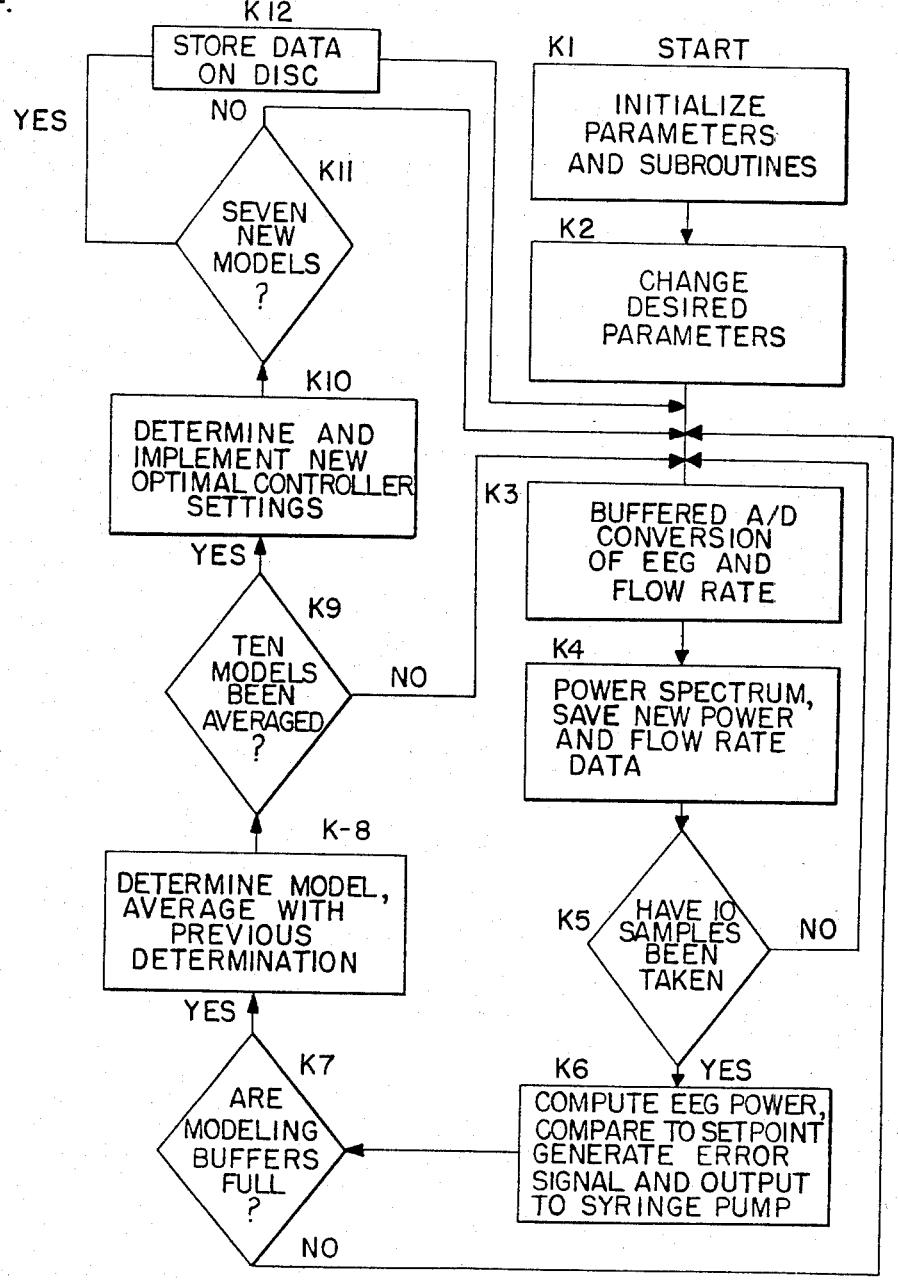
FIG. 4 is a flow diagram of a digital optimal-adaptive proportional-integral control system.

The flow chart of FIG. 4 provides a high level operational description of the control steps for the digital optimal-adaptive, proportional-integrated (DOAPI) apparatus shown in FIG. 3. This executive program shows a first section K1 used for system initialization including the functions of clearing data blocks, setting block size, and initializing various counters for the subroutines. The K2 section determines whether the operator desires the current values of operational parameters to be maintained, while the following section, K3, indicates the A/D conversion of the DOAPI input. For anesthesia control, these inputs are EEG and drug flow rate, with a sample time of 1 second. The K4 block of the flow chart indicates the first steps of data processing which obtain the power spectrum, store the drug flow rate, and store the measured physiological output signal—in this case the EEG power. The decision block K5 checks to determine whether ten one-second samples of data have been obtained. If not, a new sample is obtained and processed. When 10 samples have been processed they are averaged, and three subroutines, i.e., POWER, DGCON, and DAC are called. EEG power is obtained by the POWER subroutine; DGCON computes the error and control signal; while the DAC subroutine outputs the signal through the DAC to the servocontrolled syringe pump. These steps are indicated by the section K6. The next decision section, K7, determines if the data blocks used as the modeling buffers are full. If not, the previous loop, K3 through K6, is repeated until they are full, at which time the drug/subject system model is determined by step K8. This is repeated until ten models are averaged as shown by the section K9, whereupon new optional controller settings are computed and implemented at the section labeled K10. With a one-second sample time, a new drug/subject system model is determined every 1280 seconds, or 21 minutes and 20 seconds. After seven models have been determined, the data blocks of size 1024, used by DGCON to store data, will be full, and no more central processing unit memory is available. Therefore, DGCON reinitializes itself and these data blocks are moved to the disc, as indicated in section K12. For the most part, understanding of the twelve sections outlined above is well within the purview of the skilled programmer, and hence a discussion of the details of the subroutines is considered unnecessary.

The subroutine DGCON compares the measured output variable to the set point which generates a new value for the error signal. The integrated error (IERR) is then computed by the formula $$IERR = IERR_{old}/CIERR + ERROR$$

where:
ERRI = current value of the integrated error
$ERRI_{old}$ = previous value of the integrated error
ERROR = current value of the error
CIERR = weight given to the old integrated error
There is a DGCON safety option (OLIMT) allowing immediate cut-off of the drug input if the error is negative, i.e., if there is any overshoot. The control signal (CNTRL) is computed by:

CNTRL=PKC(ERROR+ERRI/TAUI)+CTRLK where:
PKC=controller gain
ERROR and ERRI are as defined above
TAUI=controller reset time, i.e., controller integrated-error weight
CTRLK=actuator DC bias.

The remainder of DGCON stores the new values of EEG power, error, integrated error, and control signal, and outputs optional listing(s) of their values, as determined by the operator.

An additional major subroutine is responsible for computing the optimal computer settings from the adaptive modeling which has been performed on-line by an executive program. A slight modification of conventional engineering methods (as taught in the aforementioned Cohen and Coon reference) for determining the optimal controller settings are implemented by finding the model maximum, fitting a line to the slope of the inflection point of the process reaction curve, and computing new values for proportional gain and reset time from the dead time, ultimate gain, and slope at inflection point. The particular control system and controlled variable response parameters mentioned above are readily understandable in terms of the description of the analog embodiment described in connection with FIG. 2 where the terms mentioned above were introduced. In the present context, these quantities may be considered as the digital equivalent emulations of their analog counterparts.

It is useful at this point to outline some experimental results obtained by the SAFCAD apparatus disclosed. The model anesthetic drug employed in the experimental work was sodium thiopental (Pentothal ® Sterile Powder, Abbott Laboratories). It was reconstituted to a 2% solution with saline (Normal Saline, 0.9%, Abbott Laboratories). The experimental animals were 10-week to 1 year old male New Zealand white rabbits, weighing 2 to 4 kilograms.

Four stainless-steel screw electrodes were surgically implanted in the cranium of each of the rabbits. The electrodes were constructed by fastening a gold female microconnector to an 0–80×⅛-inch flathead stainless-steel screw. Matching male microconnectors were soldered to the EEG leads. EEG was recorded from a pair of electrodes on the same side of the rabbit's skull. EEG was amplified with high frequency filter set at 30 Hz and low frequency response to 0.53 Hz. Gain was 400 µV/V output, except when predrug EEG amplitude was unusually high or low. The amplified EEG was recorded.

The measurement with sufficient sensitivity and resolution of very slow flows, such as those encountered for drug infusions, is a nontrivial problem. A venturi was constructed with a ¼-inch glass tube melted and drawn down to about 0.5 mm i.d. which provided suitable pressure drop for measurement with the sensitive differential pressure transducer (Whittaker Corp., Instrument Systems Division, Model CD10). Each venturi was calibrated for accurate measurement of the flow rate.

While the traditional pharmacokinetic modeling method consists of determining blood-level time-course response to a series of intravenous bolus doses, herein the time course of a pharmacological response was modeled. EEG response to thiopental was studied in a Latin-square experimental design with five rabbits and six dose levels. The dosages administered were placebo, 2.5, 5.0, 7.5, 10.0 and 12.5 mg/kg. Both the integral-mean-frequency ($f_{50}$) and power time courses were determined for the thiopental injections.

Figure 5A:
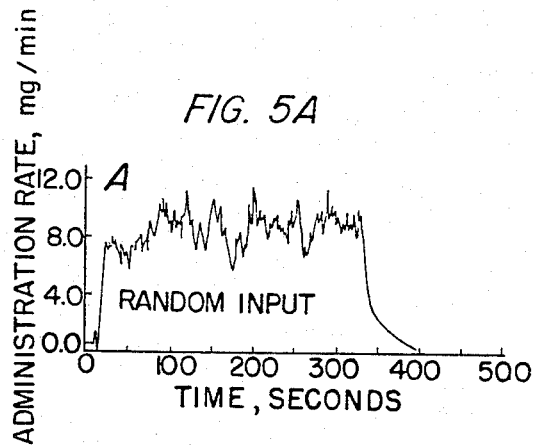
FIGS. 5A–5E are waveforms illustrating operation of the control system.
Figure 5B:
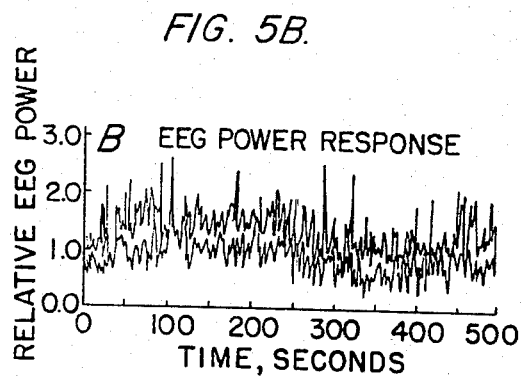
Figure 5C:
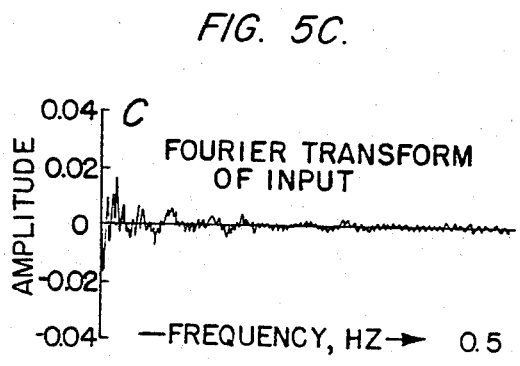
Figure 5D:
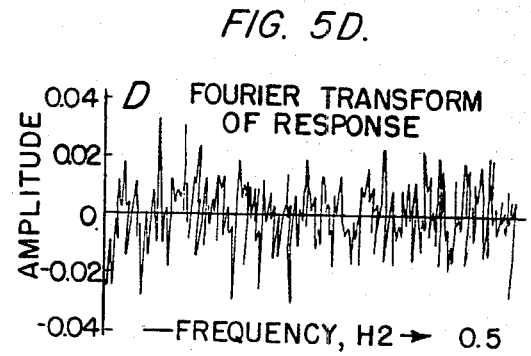
Figure 5E:
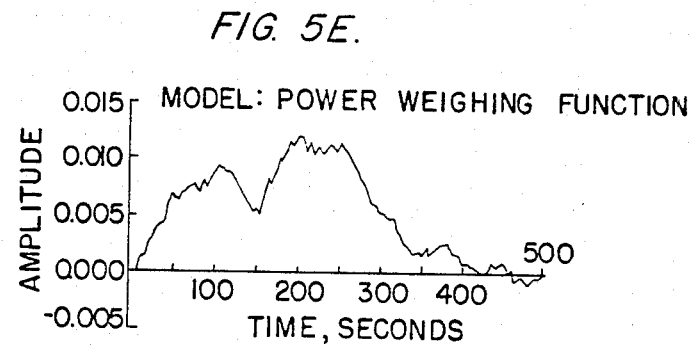

EEG response of rabbits to thiopental was modeled by input of a random flow rate of thiopental solution. This is a unique approach to pharmacokinetic modeling and is readily adaptable to on-line analysis. The random thiopental input was generated by driving the syringe pump with a pseudorandom binary signal (PRBS), which drove the syringe pump through the digital-to-analog converter (DAC). A PRBS must be filtered to produce a random signal. The rule of thumb generally used is that the maximum binary frequency should be approximately twenty times the cut-off frequency of the filter. The syringe pump itself adequately filtered the PRBS because it was a second-order system with corner frequencies at 0.052 and 0.009 Hz. Clocking frequencies of the PRBS ranged from 15 to 0.1 Hz. The best models were obtained for clocking rates of between 0.4 and 3.75 Hz. Driving signals of several frequencies were used to generate random inputs of thiopental to determine which would give the best reliable models for induction phase anesthesia. FIG. 5A shows results for a 3.75-Hz PRBS. The EEG-power response which resulted from this input is shown in FIG. 5B. The Fourier transforms (FT) of these time-varying signals are given by FIGS. 5C and 5D, respectively. The resulting model of FIG. 5E was computed by dividing the FT of the output of FIG. 10D by the FT of the input of FIG. 5C and inverting the transformation. The D.C. values in the transforms were removed to form deviation variables of the input and response.

The ultimate test of any control scheme is how well it fulfills the desired performance criteria. Therefore, the quality and duration of control were determined for each controller to compare the various controllers. With a constant i.v. infusion of thiopental, adequate, but unstable, anesthesia can be maintained for a maximum of 60 minutes, after which rapid respiratory arrest ensues. In contrast, a very constant level of anesthesia can be maintained with feedback control. Excellent control of anesthesia has been maintained repeatedly for several hours with the three SAFCADs. Control could have been extended indefinitely with any of these.

The accuracy and variability of control was determined by the integral-squared-error (ISE) performance criterion which is defined as:

$$ISE = \int_{-\infty}^{t} e^2(t)\,dt$$

where e(t)=error signal.

The ISE values are tabulated below for each of the control systems. Each value is the average of results for three to seven rabbits. From these results it is apparent that there is considerable deviation in the EEG power during constant thiopental infusions as shown by the ISE, which is greater than that for any of the feedback-control methods.

| System | Average ISE ± 1σ |
|---|---|
| DOAPI | 0.184 ± 0.088 |
| DPI | 0.231 ± 0.057 |

| System | Average ISE ± 1σ |
|---|---|
| API | 0.405 ± 0.118 |
| Constant | 0.850 ± 0.352 |

The performance of DOAPI and DPI SAFCADs clearly depends on the PI settings for the controllers. The DOAPI settings were computed from the on-line system model using the aforementioned Cohen and Coon method for optimal controller settings.

Although the invention has been described in terms of illustrative and preferred embodiments, the invention should not be deemed limited thereto, since other embodiments and modifications will readily occur to one skilled in the art. It is therefore to be understood that the appended claims are intended to cover all such modifications and changes as fall within the true spirit and scope of the invention.

What is claimed is:

1. An adaptive control system for administering a drug to a subject responsive to a drug/subject system model, comprising:
   (a) means for sensing at least one physiological parameter of said subject and for converting said at least one parameter into a corresponding response signal;
   (b) preset means for establishing a preset drug order signal;
   (c) means for administering said drug to said subject in response to an actuating signal; and
   (d) a control loop for providing said actuating signal to said means for administering, said control loop including:
   (i) comparator means for accepting first and second input signals and producing an error signal representing the difference therebetween, said comparator means being connected to said preset means for accepting said order signal as a first input thereto;
   (ii) response signal processing means connected to said sensing means for processing said response signal and for providing said processed response signal as a second input of said comparator means;
   (iii) means for sampling said response signals and rates at which drugs are administered by said means for administering;
   (iv) means for determining values for said drug/subject system model as a function of said sampled signals and rates and producing control signal information in accordance therewith;
   (v) adaptive controller means for receiving said error signal from said comparator means and said control signal information from said means for determining, said adaptive controller means translating said error signal into an actuating signal for application to said administering means in accordance with said values for said drug/subject system model defined by said control signal to optimally minimize said error signal.

2. The adaptive control system according to claim 1 wherein said response signal processing means produces a processed response signal representative of real time power associated with said physiological parameter sensed.

3. The adaptive control system according to claim 1 wherein said means for sampling and said means for determining are operative on a periodic basis to provide said adaptive controller means with time variable control signal information for optimally minimizing said error signal.

4. The adaptive control system according to claim 3 wherein said response signal processing means produces a processed response signal representative of real time power associated with said physiological parameter sensed.

5. The adaptive control system according to claim 4 wherein said adaptive controller takes the form of a proportional-integral controller having a proportional gain parameter and an integral time parameter, said parameters being automatically set to said drug/subject system model in response to said control signal information provided thereto.

6. The adaptive control system according to claim 5 wherein said drug/subject system model includes an ultimate gain parameter, a time delay parameter and a slope parameter.

7. The adaptive control system according to claim 4 wherein said adaptive controller takes the form of a proportional-integral-derivative controller having characteristic parameters set to said drug/subject system model in response to said control information.

8. The adaptive control system according to claim 1 wherein said means for administering takes the form of an infusion pump for providing a continuous flow of said drug into said subject.

9. The adaptive control system according to claim 8 wherein said adaptive controller takes the form of a proportional-integral controller having a proportional gain parameter and an integral time parameter, said parameters being automatically set to said drug/subject system model in response to said control signal information provided thereto.

10. The adaptive control system according to claim 9 wherein said drug/subject system model includes an ultimate gain parameter, a time delay parameter and a slope parameter.

11. The adaptive control system according to claim 10 wherein said adaptive controller parameters are established in substantial part by said control signal information.

12. The adaptive control system according to claim 8 wherein said adaptive controller takes the form of a proportional-integral-derivative controller having characteristic parameters set to said drug/subject system model in response to said control information.

13. The adaptive control system according to claim 1 wherein said at least one sensed physiological parameter is an EEG signal and said processed response signal corresponds to said subject's total EEG power.

14. The adaptive control system according to claim 13 wherein said drug is an anesthetic.

15. The adaptive control system according to claim 14 wherein said drug is thiopental.

16. A control system for administering a drug to a subject comprising:
   means for establishing a preset drug order signal;
   means for sensing a physiological parameter from a said subject and producing a response signal corresponding to said parameter sensed;
   means for translating said response signal into an averaged signal representing a weighted average of said physiological parameter sensed;
   means for administering said drug to said subject in response to an actuating signal;

means for comparing said preset drug order signal and said averaged signal and obtaining an error signal corresponding to a difference therebetween;

first means for processing a first portion of said error signal according to an integration function to obtain a first signal;

second means for processing a second portion of said error signal according to a proportional control function to obtain a second signal; and means for combining said first and second signals into an actuating signal and applying said actuating signal to said means for administering said drug to said subject.

17. The control system according to claim 16 wherein said averaged signal takes the form of a power signal representing power presently in said physiological parameter sensed.

18. The control system according to claim 17 wherein said means for translating said response signal comprises:

third means for processing one portion of said response signal into a third signal representing the square of the integral of said one portion of said response signal;

fourth means for processing another portion of said response signal into a fourth signal representing the integral of the square of said another portion of said response signal; and summing means for combining said third and fourth signals to form said power signal representing power present in said physiological parameter sensed.

19. The control system according to claim 18 wherein said summing means additionally acts to remove d.c. components present in said third and fourth signals.

20. The control system according to claim 19 wherein the magnitude of said response signal applied to said means for translating is adjustable.

21. The control system according to claim 19 wherein the magnitudes of each of said third and fourth signals and the relation therebetween are adjustable.

22. The control system according to claim 17 wherein said sensed physiological parameter is an EEG signal and said power signal is representative of a subject's total EEG power.

23. The control system according to claim 17 wherein said drug is an anesthetic.

24. The control system according to claim 23 wherein said drug is thiopental.

25. The control system according to claim 17 wherein said means for administering takes the form of an infusion pump for providing a continuous flow of said drug into said subject.

26. The control system according to claim 17 wherein the relation in magnitude of said first and second portions of said error signal is adjustable.

27. The control system according to claim 26 wherein said means for translating said response signal comprises:

third means for processing one portion of said response signal into a third signal representing the square of the integral of said one portion of said response signal;

fourth means for processing another portion of said response signal into a fourth signal representing the integral of the square of said another portion of said response signal; and summing means for combining said third and fourth signals to form said averaged signal representing power present in said physiological parameter sensed.

28. The control system according to claim 27 wherein said summing means additionally acts to remove d.c. components present in said third and fourth signals.

29. The control system according to claim 28 wherein the magnitudes of each of said third and fourth signals and the relation therebetween are adjustable.

30. The control system according to claim 29 wherein said sensed physiological parameter is an EEG signal and said averaged signal is representative of a subject's total EEG power.

31. The control system according to claim 30 wherein said drug is an anesthetic.

* * * * *